(12) United States Patent
Torrella et al.

(10) Patent No.: US 9,138,481 B2
(45) Date of Patent: Sep. 22, 2015

(54) CELLULOSIC GEL COMPOSITION WITH IMPROVED VISCOSITY STABILITY

(71) Applicant: Alcon Research, Ltd., Fort Worth, TX (US)

(72) Inventors: Gemma Torrella, Barcelona (ES); Guadalupe Almera, Barcelona (ES); Jordi Garcés, Barcelona (ES)

(73) Assignee: Alcon Research, Ltd., Fort Worth, TX (US)

( * ) Notice: Subject to any disclaimer, the term of this patent is extended or adjusted under 35 U.S.C. 154(b) by 0 days.

(21) Appl. No.: 13/687,315

(22) Filed: Nov. 28, 2012

(65) Prior Publication Data

US 2013/0142837 A1 Jun. 6, 2013

Related U.S. Application Data

(60) Provisional application No. 61/567,294, filed on Dec. 6, 2011.

(51) Int. Cl.
| | | |
|---|---|---|
| *A61K 47/38* | (2006.01) | |
| *A61K 9/00* | (2006.01) | |
| *A61K 9/06* | (2006.01) | |

(52) U.S. Cl.
CPC ............... *A61K 47/38* (2013.01); *A61K 9/0048* (2013.01); *A61K 9/06* (2013.01)

(58) Field of Classification Search
None
See application file for complete search history.

(56) References Cited

U.S. PATENT DOCUMENTS

| | | | | |
|---|---|---|---|---|
| 5,888,493 | A * | 3/1999 | Sawaya ...................... | 424/78.04 |
| 2003/0203034 | A1 * | 10/2003 | Huth ............................. | 424/487 |
| 2007/0031362 | A1 * | 2/2007 | Kreeger et al. ............ | 424/70.13 |
| 2007/0128156 | A1 | 6/2007 | Chowhan et al. | |
| 2008/0226724 | A1 | 9/2008 | Ji et al. | |
| 2009/0131303 | A1 * | 5/2009 | Hong et al. ....................... | 514/6 |
| 2009/0209574 | A1 | 8/2009 | Owen et al. | |
| 2010/0216700 | A1 * | 8/2010 | Li et al. ............................ | 514/11 |

FOREIGN PATENT DOCUMENTS

| | | |
|---|---|---|
| WO | 0018386 | 4/2000 |
| WO | 2009/111418 | 9/2009 |
| WO | 2011/028718 | 3/2011 |
| WO | 2011/127196 | 10/2011 |

OTHER PUBLICATIONS

Aqualon Ethylcellulose (EC) Physical and Chemical Properties' A speciality polymer; Hercules; 2002.
PCT International Preliminary Report on Patentability for corresponding International Application No. PCT/US2012/066799 with mailing date Jun. 19, 2014, 8 pages.
Dahl et al., 1998, "Effect of Hydrogen peroxide on the Viscosity of a Hydroxyethylcellulose-Based Gel", Pharmaceutical Research, vol. 15, No. 7, pp. 1137-1140.
Ji et al., 2009, "Effect of EDTA and Methionine on Preventing Loss of Viscosity of Cellulose-Based Topical Gel", AAPS PharmSciTech, vol. 10, No. 2, pp. 678-683.
PCT International Search Report for corresponding International application No. PCT/US2012/066799 with mailing date Mar. 11, 2013, 4 pages.
PCT Written Opinion for corresponding International application No. PCT/US2012/066799 with mailing date Mar. 11, 2013, 6 pages.
Torrents, Jordi Garcés, Jun. 6, 2011, "Analysis of two ophthalmic gels by Triple Detection Gel Permeation Chromatography", Malvern report, pp. 1-21.

\* cited by examiner

*Primary Examiner* — Robert A Wax
*Assistant Examiner* — Randeep Singh
(74) *Attorney, Agent, or Firm* — Scott A. Chapple

(57) ABSTRACT

The present invention is directed to cellulosic gel compositions having improved viscosity stability through the exclusion of particular antioxidants and/or the exclusion of chemical entities that tend to produce free radicals. Preferably, the composition is an ophthalmic cellulosic gel composition that is suitable as a multi-dose composition.

24 Claims, 5 Drawing Sheets

US 9,138,481 B2

CELLULOSIC GEL COMPOSITION WITH IMPROVED VISCOSITY STABILITY

CROSS-REFERENCE TO RELATED APPLICATION

The present application claims priority based on U.S. Provisional Patent Application Ser. No. 61/567,294 filed Dec. 6, 2011.

TECHNICAL FIELD OF THE INVENTION

The present invention is related to a cellulosic gel composition (particularly an ophthalmic composition) that maintains improved viscosity stability through the exclusion of particular antioxidants and/or the exclusion of chemical entities that tend to produce free radicals.

BACKGROUND OF THE INVENTION

The pharmaceutical industry, the cosmetic industry and other industries have long been concerned with the formation of gel products that have viscosity stability. In particular, these industries have spent significant resources in developing gel products that maintain substantially the same viscosity over extended periods of time.

A great many different viscosity or gelling agents have been discovered and used in a wide variety of products. These viscosity agents include, without limitation, carboxyvinyl polymers, gums (e.g., xanthan gum), sodium hyaluronate, cellulosics (e.g., hydroxyethyl cellulose (HEC) and hydroxypropylmethyl cellulose (HPMC)), polyethylene glycol and the like. For nearly all of these viscosity agents, it has been found that free radicals tend to inhibit their ability to maintain viscosity of their respective compositions. In particular, free radicals tend to initiate oxidation reactions, which ultimately release additional free radicals, which then cause further oxidation reactions. This oxidation reaction cycle then degrades the viscosity agents and degrades the ability of the viscosity agents to maintain viscosity or the compositions.

To combat the degradation of viscosity agents through oxidation reactions, the various industries have focused upon the use of anti-oxidants that act as free radical scavengers. These anti-oxidants act to lower the number of free radicals in the composition and, in turn, lower the number of oxidation reactions occurring in the composition.

Anti-oxidants are generally effective in limiting oxidation reactions and are effective for aiding in maintaining viscosity stability of the overall composition. However, it has also been more recently discovered that many of the anti-oxidants themselves tend to lower viscosity of at least some of compositions albeit typically significantly less than would be caused by the oxidation reactions, which the anti-oxidants prevent.

Cellulosic ether viscosity enhancers (e.g., HPMC and HEC) are susceptible to degradation since these cellulosics typically include peroxy free radicals as impurities. Of course, these peroxy free radicals can initiate oxidation reactions, which can degrade these viscosity agents. However, it has been surprisingly discovered by the inventors of the present invention that, in particular compositions, antioxidants such as ion chelators, particularly ethylenediaminetetraacetic acid (EDTA), tend to significantly reduce viscosity of cellulosic ethers, particularly HEC, over time. Further, it has been discovered that, in these particular compositions, cellulosic ethers, particularly HEC, tends to maintain its viscosity quite well in the absence of any antioxidant.

SUMMARY OF THE INVENTION

The present invention is directed to a composition (e.g., a multi-dose ophthalmic composition) that includes cellulosic polymer at a concentration sufficient by itself to gel the composition. The cellulosic polymer is preferably substantially entirely cellulosic ether polymer. It is also preferable for the composition to include therapeutic agent. The composition is substantially free of any anti-oxidant that would otherwise act as a free radical scavenger and inhibit oxidation reactions within the composition and the composition typically has a pH between 6.0 and 8.5. A preferred cellulosic polymer is hydroxyethyl cellulose.

In a preferred embodiment, the composition is substantially free of any chemical entity, other than the cellulosic polymer along with its impurities that produces any significant amount of free radicals where those free radicals would normally degrade the cellulosic polymer within the composition through oxidation reactions.

The present invention is also directed to a multi-dose ophthalmic product that includes a tube with an ophthalmic composition disposed within the tube. The ophthalmic composition will typically include the characteristics discussed above. Preferably, the tube is configured for dispensing individual strips of the composition topically to the eye.

DETAILED DESCRIPTION OF THE INVENTION

Figure 1:
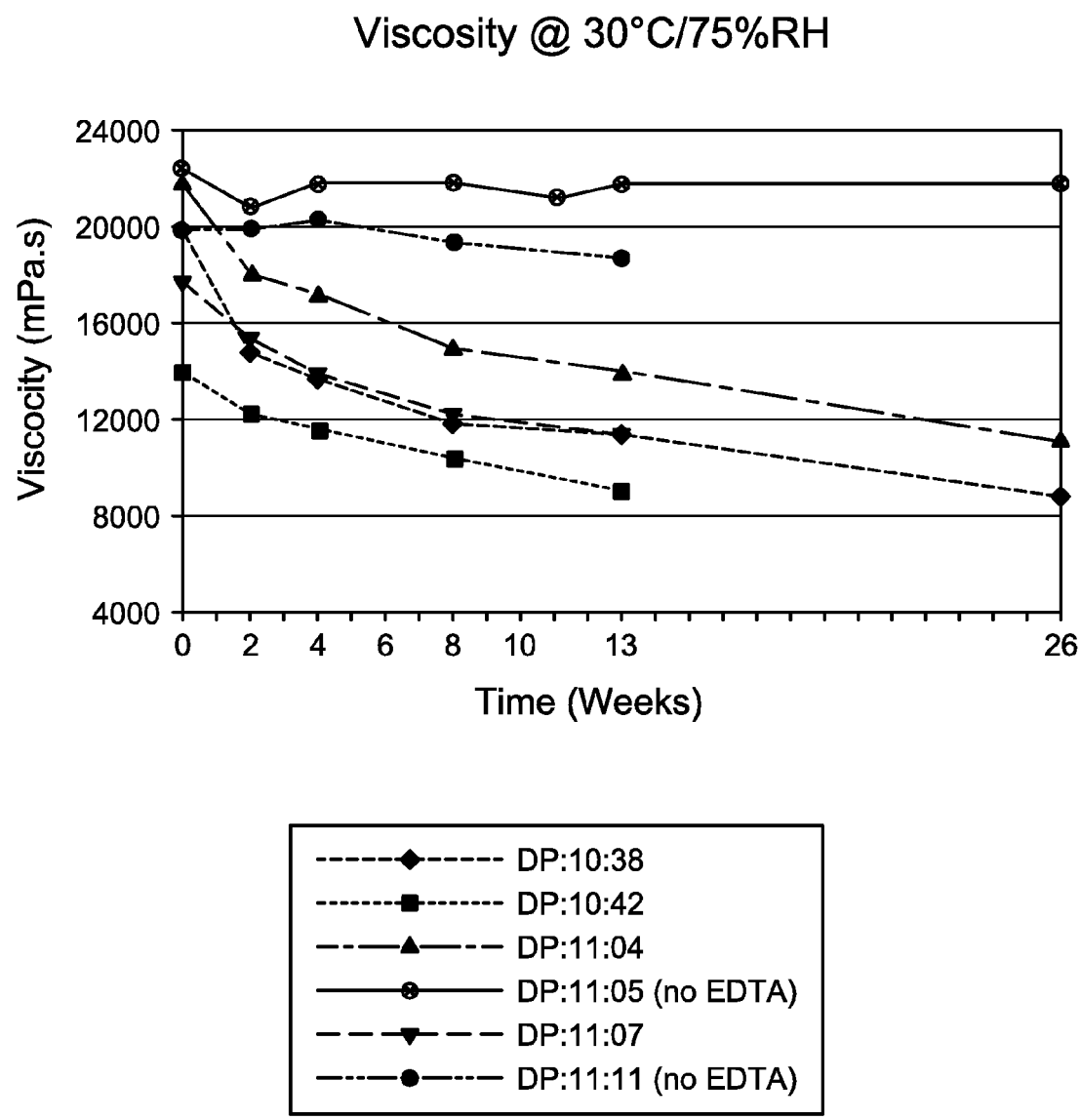
FIG. 1 is a chart of viscosity data of ophthalmic gels both with and without EDTA after storage at 30° C.

The present invention is predicated upon the provision of a gel composition and particularly an ophthalmic gel composition that substantially maintains its viscosity over an extended period of time. The composition includes cellulosic polymer as a gelling agent. The cellulosic polymer is typically provided within the composition at a concentration that allows the cellulosic polymer to gel the composition by itself. The composition is substantially free of any anti-oxidant that would otherwise act as a free radical scavenger and inhibit oxidation reactions within the composition. The composition will also typically include therapeutic agent, although not necessarily required unless otherwise specifically stated.

Unless otherwise indicated, percentages provided for the ingredients of the ophthalmic composition of the present invention are weight/weight (w/w) percentages.

Unless otherwise stated, viscosity measurement are taken 25° C. using a Brookfield DV-II+viscometer, SC-14 Spindle at 20 RPM for 1 minute.

The cellulosic polymer may be a single cellulosic polymer or may be a combination of two or more cellulosic polymers.

Preferably, the term "cellulosic polymer" as used herein, represents any and all cellulosic polymers present in the composition. Highly preferred cellulosic polymers are cellulosic ethers. Thus, in a preferred embodiment, the cellulosic polymer is substantially entirely (i.e., at least 70% and more preferably at least 90% by weight) or entirely one or more polymeric cellulosic ether[s].

Examples of suitable cellulosic polymers include, without limitation, hydroxyethyl cellulose (HEC), hydroxypropylmethyl cellulose (HPMC), methylethyl cellulose (MEC), carboxymethyl cellulose (CMC), any combination thereof or the like. The cellulosic polymer is typically present in the composition at a concentration of at least 0.5%, more typically at least 0.9% and even more typically at least 1.7% and even possibly at least 2.5%. The cellulosic polymer is also typically present in the composition at a concentration of no greater than 10%, more typically no greater than 6%, even more typically no greater than 4% and even possibly no greater than 3.5%. Of course, the particular concentration of the cellulosic polymer can depend upon the particular polymer or combination of polymers in the composition.

As suggested above, it is preferable that the cellulosic polymer be capable of gelling the composition by itself. Specifically, this means that the removal of the cellulosic polymer from the composition would allow the composition to become a solution. As used herein the term "gel" is meant to suggest that the composition has a viscosity of at least 2000 millipascals-seconds (mPa·s), more typically at least 4000 mPa*s, even more typically at least 8000 mPa*s and even possibly at least 12000 or even 18000 mPa*s at 20° C. Thus, the cellulosic polymer is provided in the composition at a concentration that typically raises the viscosity (taken at 25° C.) of the composition at least 3000 mPa*s, more typically at least 5000 mPa*s and even more typically at least 9000 mPa*s or 10000 mPa*s relative to a comparison composition having the exact same ingredients as the composition, but excluding the cellulosic polymer. The overall viscosity of the composition is typically at least 5000 mPa*s more typically at least 8000 mPa*s and even more typically at least 10000 mPa*s or 14000 mPa*s, but is typically at a concentration no greater than 60000 mPa*s more typically no greater than 35000 mPa*s and even more typically no greater than 25000 mPa*s.

One highly preferred cellulosic polymer is HEC. It may be used alone or in combination with another cellulosic polymer. In a preferred embodiment, HEC is at least 50% by weight, more typically at least 70% by weight and even more typically at least 90% by weight of the cellulosic polymer in the composition. In a highly preferred embodiment, the cellulosic polymer consists or consists essentially of HEC or, in other words, is substantially entirely (i.e., at least 95% by weight) or entirely REC. In these embodiments, the HEC is typically present in the composition at a concentration that is at least 2.0%, more typically at least 2.6% and even more typically at least 2.85%, but is typically at a concentration no greater than 5.0%, more typically no greater than 4.0% and even more typically no greater than 3.3%. The average molecular weight of the preferred HEC is typically at least $1 \cdot 10^4$ more typically at least $1 \cdot 10^5$ and even more typically at least $1 \cdot 10^6$, but is typically no greater than $1 \cdot 10^8$, more typically no greater than $1 \cdot 10^7$ and even more typically no greater than $2 \cdot 10^6$. One particularly preferred HEC is NATROSOL 250HX, commercially available from Ashland Inc., Covington, Ky.

The composition is substantially free or entirely free of any anti-oxidant that would otherwise act as a free radical scavenger and inhibit oxidation reactions within the composition. As used herein, the phrase "substantially free of any oxidant that would otherwise act a free radical scavenger" means that the composition includes less than 0.0001% of any such anti-oxidant. The phrase "anti-oxidant that would otherwise act as a free radical scavenger and inhibit oxidation reactions" means that the anti-oxidant can neutralize free radicals by accepting or donating an electron or can chelate metals to prevent metallic-catalyzed oxidation. Such anti-oxidants include, without limitation, ion chelators such as ethylenediaminetetraacetic acid (EDTA), ascorbic acid and derivatives thereof, tocopherols, sulfurous acid salts such as sodium sulfite or sodium bisulfite, thiol derivatives such as cysteine, butylated hydroxyanisole (BHA), butylated hydroxytoluene (BHT), any combinations thereof or the like.

In one embodiment, the composition be substantially free of any chemical entity, other than the cellulosic polymer and any of its impurities, that provides any significant amount of free radicals, which would normally degrade the cellulosic polymer within the composition through oxidation reactions. As used herein, the phrase "significant amount of free radicals" is intended to mean any amount of free radicals that is greater than the amount of free radicals provided by the cellulosic polymer and its impurities. As a quantity, the composition is preferably free of any chemical entity that provides free radicals, particularly peroxy radicals, in a concentration greater than 10 ppm, more typically greater than 5 ppm, even more typically greater than 3 ppm and even possibly greater than 1 ppm.

It has also been recognized that the lack of anti-oxidant in the compositions of the present application seems to aid the compositions in maintaining their viscosity despite the inclusion of the type of five radicals discussed above. Thus, in one embodiment, it is contemplated that the composition includes a chemical entity (e.g., hydrogen peroxide) at a concentration of at least 5 ppm, more typically at least 10 ppm, more typically at least 50 ppm but typically no greater than 1000 ppm and more typically no greater than 400 ppm.

An effective amount of therapeutic agent is preferably included in the composition of the present invention. The therapeutic agent can include a single therapeutic agent or two or more therapeutic agents. Example of some potential classes of therapeutic agents include, without limitation, antibiotics, ant-inflammatories and the like. As suggested above and discussed below, however, the composition of the present invention is particularly useful as an ophthalmic composition. As such, the therapeutic agent will typically include one or more ophthalmic drugs.

Non-limiting examples of potential ophthalmic therapeutic agents for the present invention include: anti-glaucoma agents, anti-angiogenesis agents; anti-infective agents; anti-inflammatory agents; growth factors; immunosuppressant agents; and anti-allergic agents. Anti-glaucoma agents include beta-blockers, such as betaxolol and levobetaxolol; carbonic anhydrase inhibitors, such as brinzolamide and dorzolamide; prostaglandins, such as travoprost, bimatoprost, and latanoprost; seretonergics; muscarinics; dopaminergic agonists. Anti-angiogenesis agents include anecortave acetate (RETAANE™, Alcon™ Laboratories, Inc. of Fort Worth, Tex.) and receptor tyrosine kinase inhibitors (RTKi). Anti-inflammatory agents include non-steroidal and steroidal anti-inflammatory agents, such as triamcinolone actinide, suprofen, diclofenac, ketorolac, dexamethasone, nepafenac, rimexolone, and tetrahydrocortisol. Growth factors include EGF or VEGF. Anti-allergic agents include olopatadine and epinastine. Anti-infectives include moxifloxacin, tobramycin and ciprofloxacin. The ophthalmic drug may be present in the form of a pharmaceutically acceptable salt. The concentrations of these therapeutic agents can vary depending upon the particular agent, but the concentration will typically be at least 0.0001, but no greater than 4.0%.

In one preferred embodiment, the composition includes an anti-infective moxifloxacin) and/or a steroidal (e.g., dexamethasone). When included, the anti-infective will typically be in the composition at a concentration that is at least 0.04% more typically at least 0.20% and even more typically at least 0.38%, but is typically at a concentration no greater than 2.0% more typically no greater than 1.0% and even more typically no greater than 0.7%. When included, the steroidal will typically be in the composition at a concentration that is at least 0.005% more typically at least 0.02% and even more typically at least 0.05%, but is typically at a concentration no greater than 0.40% more typically no greater than 0.14% and even more typically no greater than 0.09%.

The composition can also include a buffering agent. In a preferred embodiment, the composition includes borate as a buffering agent and/or and antimicrobial aid. As used herein, the term "borate" shall refer to boric acid, salts of boric acid, borate derivatives and other pharmaceutically acceptable borates, or combinations thereof. Most suitable are: boric acid, sodium borate, potassium borate, calcium borate, magnesium borate, manganese borate, and other such borate salts. Advantageously, borate may aid in preserving the composition as well. When included, the buffering agent, particularly when it is borate, is typically in the composition at a concentration that is at least 0.05% more typically at least 0.1% and even more typically at least 0.25%, but is typically at a concentration no greater than 2.0% more typically no greater than 1.0% and even more typically no greater than 0.7% and even possibly no greater than 0.4%.

In addition to the above, it is contemplated that the composition of the present invention may contain various types of pharmaceutical excipients. Examples include, without limitation, surfactants, osmolality enhancing agent (e.g., sodium chloride), anti-microbial agents (e.g., benzalkonium chloride or polymeric quaternary ammonium compound), pH adjusting agents (e.g., HCl, NaOH), polyols or others.

The composition of the present invention will typically substantially maintain its viscosity over an extended period of time. The composition will typically lose less than 25%, more typically less than 15% and even more typically less than 10% and even possibly less than 5% of its viscosity over a period of at w least 5 days, more preferably at least 15 days and even more preferably at least 45 days and still more preferably at least 90 or even 120 days.

As discussed above, the composition of the present invention is particularly desirable as an ophthalmic composition. The present invention can be directed to the provision of multi-dose ophthalmic compositions in connection with the treatment of conditions wherein the cornea or adjacent ocular tissues are irritated, or conditions requiring frequent application of a composition, such as in the treatment of dry eye patients. The compositions of the present invention can be useful in the field of artificial tears, ocular lubricants, and other compositions used to treat dry eye conditions, as well as other conditions involving ocular inflammation or discomfort. The compositions may also be particularly useful for treating ocular infections.

The compositions of the present invention will generally be formulated as sterile gels. The compositions of the present invention are also formulated so as to be compatible with the eye and/or other tissues to be treated with the compositions. The ophthalmic compositions intended for direct application to the eye (the cornea or other portion of the eyeball) will be formulated so as to have a pH and tonicity that are compatible with the eye.

The compositions will typically have a pH in the range of 4 to 9, preferably 5.5 to 9.0, and most preferably 6.0 to 8.5. Particularly desired pH ranges are 6.5 to 8.5 and more specifically 7.5 to 8.3. The compositions will have an osmolality of 200 to 400 or 450 milliosmoles per kilogram (mOsm/kg), more preferably 240 to 360 mOsm/kg.

The composition of the present invention will typically be aqueous and include a substantial amount of water. The composition will typically have a concentration of water that is at least 50%, more typically at least 75%, more typically at least 90% and even possibly at least 93%.

The present invention is particularly desirable as a multi-dose ophthalmic composition that has sufficient antimicrobial activity to allow the compositions to satisfy the USP preservative efficacy requirements, as well as other preservative efficacy standards for aqueous pharmaceutical compositions.

The preservative efficacy standards for multi-dose ophthalmic solutions in the U.S. and other countries/regions are set forth in the following table:

| | Preservative Efficacy Test ("PET") Criteria (Log Order Reduction of Microbial Inoculum Over Time | |
|---|---|---|
| | Bacteria | Fungi |
| USP 34 | A reduction of 1 log (90%), by day 7; 3 logs (99.9%) by day 14; and no increase after day 14 | The compositions must demonstrate over the entire test period, which means no increases of 0.5 logs or greater, relative to the initial inoculum. |
| Japan | 3 logs by 14 days; and no increase from day 14 through day 28. | No increase from initial count at 14 and 28 days |
| Ph. Eur. A[1] Ver. 7 | A reduction of 2 logs (99%) by 6 hours; 3 logs by 24 hours; and no recovery after 28 days | A reduction of 2 logs (99%) by 7 days, and no increase thereafter |
| Ph. Eur. B Ver. 7 | A reduction of 1 log at 24 hours; 3 logs by day 7; and no increase thereafter | A reduction of 1 log (90%) by day 14, and no increase thereafter |
| FDA/ ISO 14730 | A reduction of 3 logs from initial challenge at day 14; and a reduction of 3 logs from rechallenge | No increase higher than the initial value at day 14, and no increase higher than the day 14 rechallenge count through day 28. |

[1]There are two preservative efficacy standards in the European Pharmacopoeia "A" and "B".

When provided as an ophthalmic composition, the composition will typically be disposed in a tube suitable for administration of the composition to the eye. The tube is typically configured for releasing strips (e.g., ribbon-like strips) of the gel topically to the eye.

Applicants specifically incorporate the entire contents of all cited references in this disclosure. Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

Other embodiments of the present invention will be apparent to those skilled in the art from consideration of the present specification and practice of the present invention disclosed herein. It is intended that the present specification and examples be considered as exemplary only with a true scope and spirit of the invention being indicated by the following claims and equivalents thereof.

Table A below provides a listing of exemplary ingredients suitable for an exemplary preferred composition of the ophthalmic composition of the present invention and a desired weight/weight percentage for those ingredients.

TABLE A

| Ingredient | w/w percent |
|---|---|
| Therapeutic Agent | 0.01, 0.1 or 1.0 |
| Cellulosic Polymer (HEC) | 3.0 |
| Boric Acid | 0.3 |
| Sodium Chloride | 0.5 |
| Preservative | 0.005 or 0.001 |
| NaOH or HCL | sufficient to achieve pH = 7.9 |
| purified water | Q.S. 100 |

It is understood that the weight/weight percents in table A can be varied by ±10%, ±20%, ±30%, ±90% of those weight/weight percents or more and that those variances can be specifically used to create ranges for the ingredients of the present invention. For example, an ingredient weight/weight percent of 10% with a variance of ±20% means that the ingredient can have a weight/weight percentage range of 8 to 12 w/w %. It is also understood that some of the ingredients may not be necessary for the composition while other ingredients may be added to the composition.

The following examples are presented to further illustrate selected embodiments of the present invention and compositions for comparison. The compositions shown in the examples were prepared using procedures that are well-known to persons of ordinary skill in the field of ophthalmic pharmaceutical compositions.

TABLE 1

Gel Compositions (Hydroxyethyl cellulose based hydrogels) with and without EDTA
Composition % (w/w)

| | A | B | C |
|---|---|---|---|
| Batches | DP:10:38 DP:10:42 | DP:11:04 DP:11:07 | DP:11:05 DP:11:11 |
| Ingredients | | | |
| Moxifloxacin HCl | 0.545 g$^{(1)}$ | 0.545 g$^{(1)}$ | 0.545 g$^{(1)}$ |
| Dexamethasone Sodium Phosphate | 0.11 g$^{(2)}$ | 0.11 g$^{(2)}$ | 0.11 g$^{(2)}$ |
| Natrosol 250 HX | 3.0 g | 3.0 g | 3.0 g |
| Sodium Chloride | 0.5 g | 0.5 g | 0.5 g |
| Boric Acid | 0.3 g | 0.3 g | 0.3 g |
| EDTA | 0.01 g | 0.01 g | — |
| Benzalkonium chloride | 0.005 g | — | — |
| Sodium Hydroxide | q.s. pH 7.9 | q.s. pH 7.9 | q.s. pH 7.9 |
| Hydrochloric Acid | q.s. pH 7.9 | q.s. pH 7.9 | q.s. pH 7.9 |
| Purified Water | q.s. 100 g | q.s. 100 g | q.s. 100 g |

Figure 2:
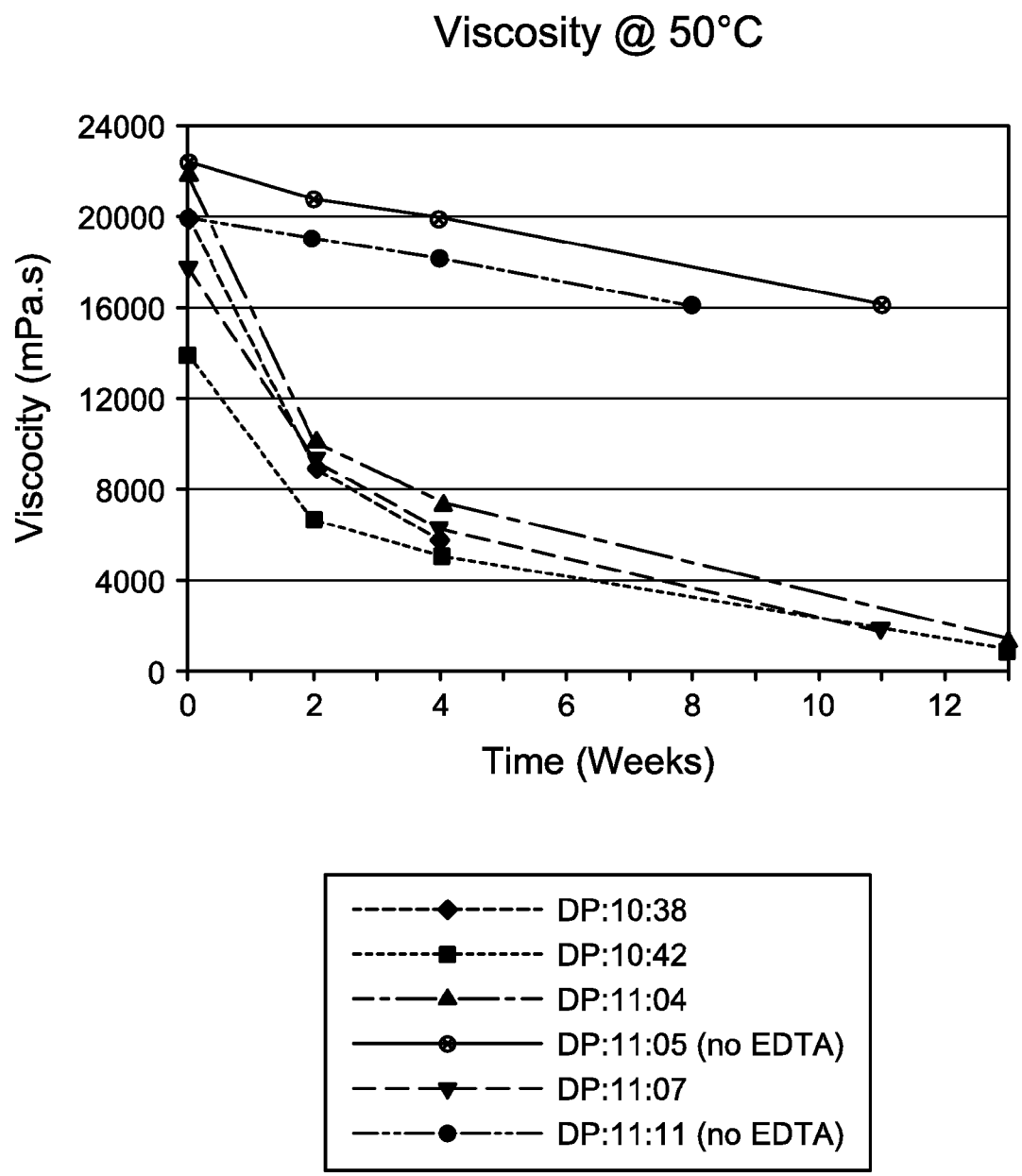
FIG. 2 is another chart of viscosity data of ophthalmic gels both with and without EDTA after storage at 50° C.

$^{(1)}$Equivalent to 0.5% Moxifloxacin base.
$^{(2)}$Equivalent to 0.1% Desamethasone Phosphate In Table 1, composition A includes both benzalkonium chloride (BAK) and EDTA, composition B is substantially identical to composition A with the exception that BAK has been removed and composition C is substantially identical to composition B with the exception that EDTA has been removed. Two batches of each of compositions A, B and C were formed and viscosity data were gathered after storage at 30° C./75% relative humidity (RH) and at 50° C. for each of the batches over a significant time period. Those data were plotted in the charts in FIGS. 1 and 2. As can be seen, removal of EDTA allowed composition C to maintain its viscosity over time significantly better than compositions A and B.

Figure 3:
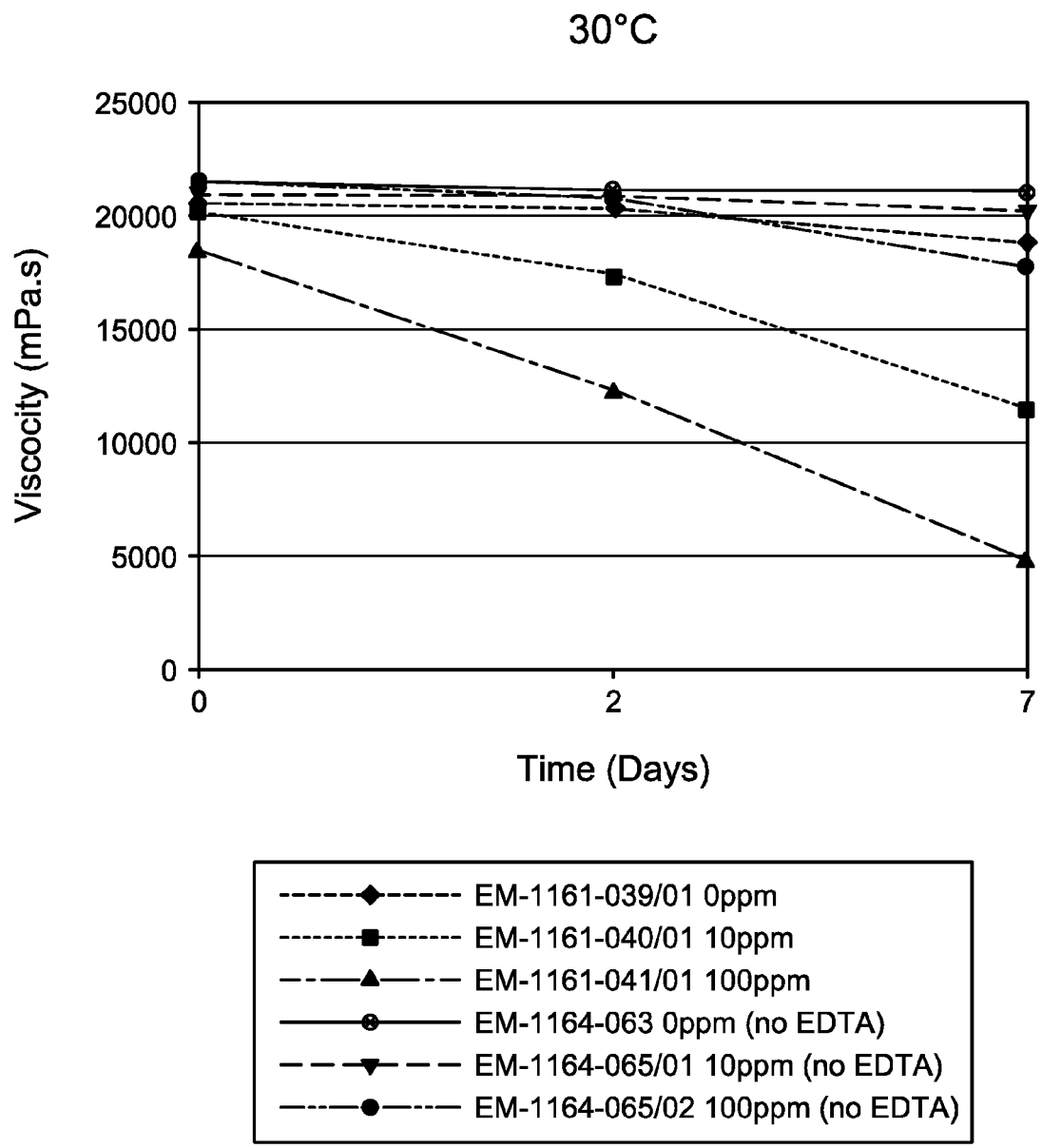
FIG. 3 is a chart of viscosity data of ophthalmic gels having various different amounts of hydrogen peroxide and being with or without EDTA after storage at 30° C.
Figure 4:
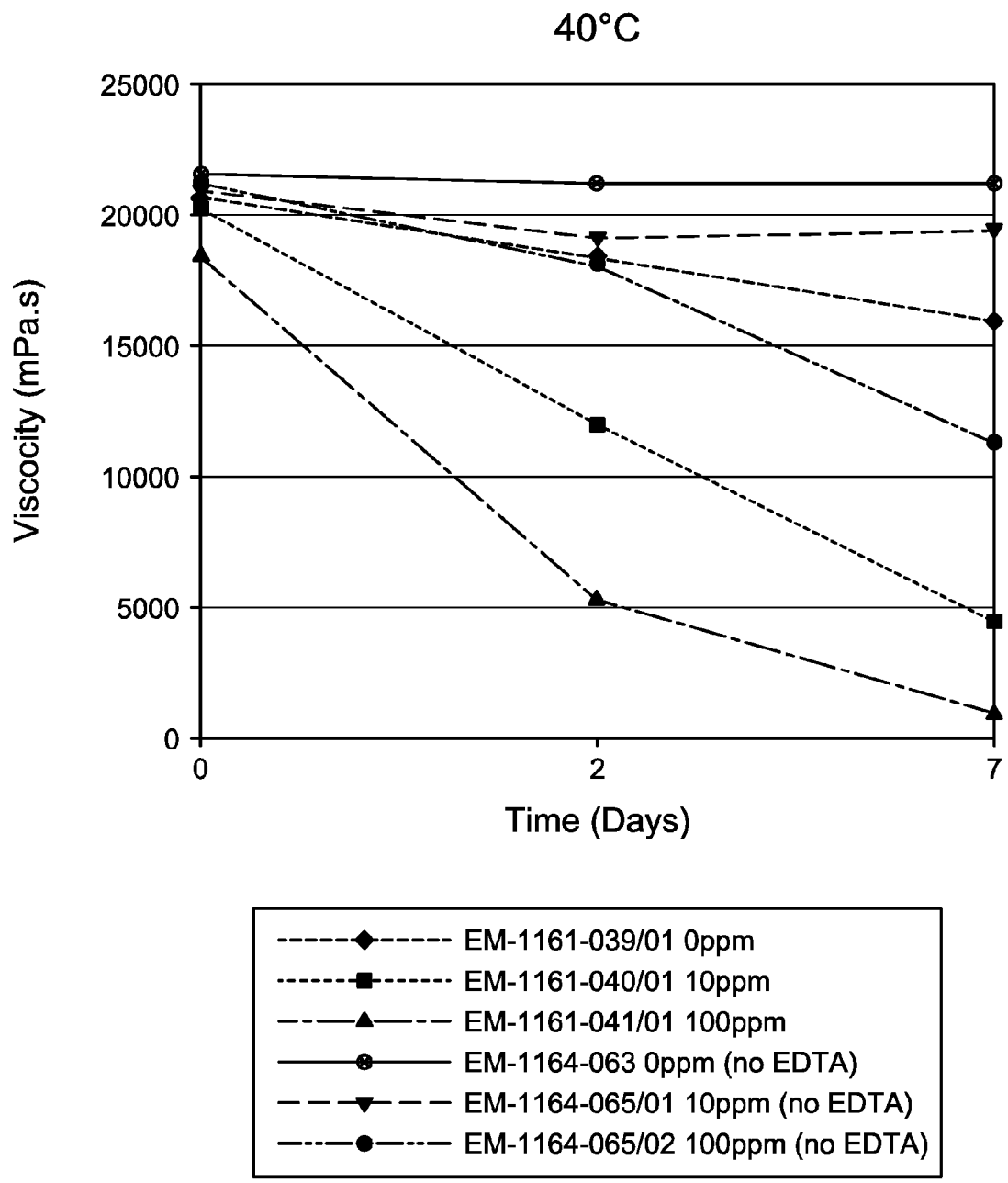
FIG. 4 is another chart of viscosity data of ophthalmic gels having various different amounts of hydrogen peroxide and being with or without EDTA after storage at 40° C.
Figure 5:
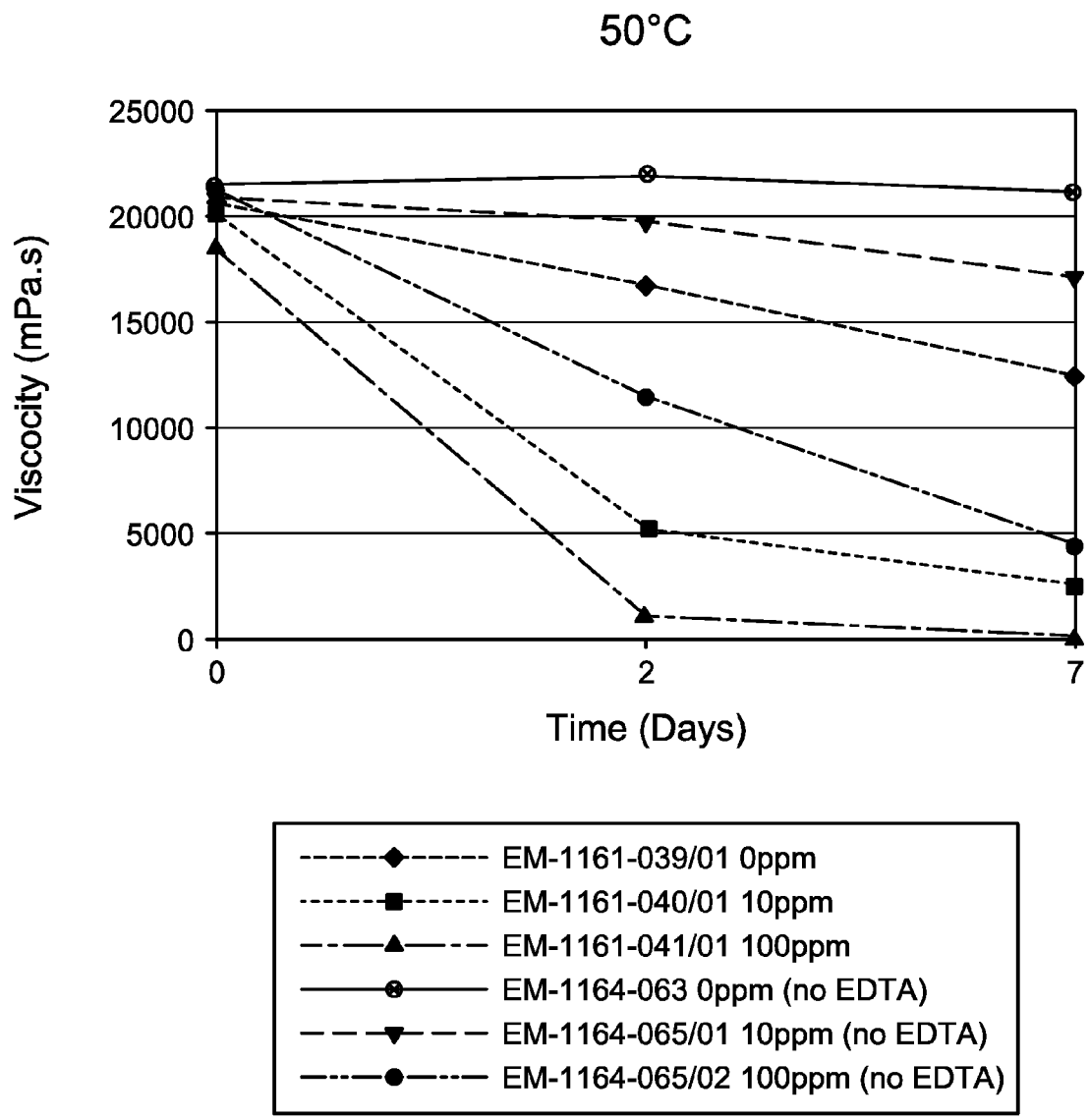
FIG. 5 is another chart of viscosity data of ophthalmic gels having various different amounts of hydrogen peroxide and being with or without EDTA after storage at 50° C.

With reference to FIGS. 3, 4 and 5, compositions substantially identical to compositions B and C of table 1 were provided and were tested under oxidative conditions while control compositions were not subjected to such oxidative conditions. Hydrogen peroxide was provided to the non-control compositions at 10 ppm and 100 ppm and viscosity data was gathered at 30° C., 40° C. and 50° C. under the hydrogen peroxide oxidative conditions to show the effect of EDTA on viscosity under such conditions. As can be seen, the compositions without the EDTA maintain their viscosity over time better than those with EDTA.

TABLE 2

Hydroxyethyl cellulose based high viscous gels

| INGREDIENTS | 0.5% Moxifloxacin 0.1% Dexamethasone Phosphate Ophthalmic Gel D | 0.5% Moxifloxacin 0.075% Dexamethasone Phosphate Ophthalmic Gel E | 0.5% Moxifloxacin 0.05% Dexamethasone Phosphate Ophthalmic Gel F |
|---|---|---|---|
| Moxifloxacin HCl | 0.545 g$^{(1)}$ | 0.545 g$^{(1)}$ | 0.545 g$^{(1)}$ |
| Dexamethasone Sodium Phosphate | 0.11 g$^{(2)}$ | 0.082 g$^{(3)}$ | 0.055 g$^{(4)}$ |
| Natrosol 250 Hx Pharma (HEC) | 3.0 g | 3.0 g | 3.0 g |
| Sodium Chloride | 0.5 g | 0.5 g | 0.5 g |
| Boric acid | 0.3 g | 0.3 g | 0.3 g |
| Sodium Hydroxide | q.s. to pH 7.9 | q.s. to pH 7.9 | q.s. to pH 7.9 |
| Hydrochloric Acid | q.s. to pH 7.9 | q.s. to pH 7.9 | q.s. to pH 7.9 |
| Purified water | q.s. to 100 g | q.s. to 100 g | q.s. to 100 g |

$^{(1)}$ Equivalent to 0.5% Moxifloxacin
$^{(2)}$ Equivalent to 0.1% Dexamethasone Phosphate
$^{(3)}$ Equivalent to 0.075% Dexamethasone Phosphate
$^{(4)}$ Equivalent to 0.05% Dexamethasone Phosphate Table 2 includes compositions D, E and F, which are illustrative of compositions of the present invention.

We claim:

1. A multi-dose ophthalmic composition, comprising: therapeutic agent; and
an aqueous vehicle consisting essentially of:
   i) cellulosic polymer at a concentration sufficient by itself to gel the composition wherein the cellulosic polymer is substantially entirely cellulosic ether polymer;
   ii) one or any combination of excipients selected from the group consisting of borate, tonicity agent and preservative;
   iii) pH adjusting agent; and
   iv) water;
wherein:
   i) the composition is substantially free of any anti-oxidant;
   ii) the composition has a pH between 6.0 and 8.5; and
   iii) the viscosity of the composition is at least 5000 mPa*s but no greater than 60000 mPa*s taken at 25° C.

2. An ophthalmic composition as in claim 1 wherein the cellulosic polymer includes hydroxyethyl cellulose.

3. An ophthalmic composition as in claim 1 wherein the cellulosic polymer is substantially entirely hydroxyethyl cellulose.

4. An ophthalmic composition as in claim 3 wherein the concentration of the HEC in the composition is at least 2.6% but no greater than 4.0%.

5. An ophthalmic composition as in claim 1 wherein the therapeutic agent includes a fluouroquinolone.

6. An ophthalmic composition as in claim 4 wherein the therapeutic agent is moxifloxacin.

7. An ophthalmic composition as in claim 1 wherein the therapeutic agent includes a steroidal anti-inflammatory.

8. An ophthalmic composition as in claim 1 wherein the therapeutic agent is dexamethasone.

9. An ophthalmic composition as in claim 1 wherein the composition is substantially free of any chemical entity, other than the cellulosic polymer along with its impurities that produces any significant amount of free radicals, which would normally degrade the cellulosic polymer within the composition through oxidation reactions.

10. An ophthalmic composition as in claim 1 wherein the concentration of the cellulosic polymer in the composition is at least 1.7% but no greater than 6%.

11. A product as in claim 1 wherein the therapeutic agent includes a fluouroquinolone.

12. A product as in claim 1 wherein the therapeutic agent includes a steroidal anti-inflammatory.

13. A product as in claim 1 wherein the concentration of the cellulosic polymer in the composition is at least 1.7% but no greater than 6%.

14. A product as in claim 1 wherein the viscosity of the composition is typically at least 8000 mPa*s but no greater than 35000 mPa*s taken at 25° C.

15. An ophthalmic composition as in claim 1 wherein the therapeutic agent includes moxifloxacin and dexamethasone.

16. An ophthalmic composition as in claim 4 wherein the therapeutic agent includes moxifloxacin and dexamethasone.

17. A multi-dose ophthalmic product, comprising:
a tube;
an ophthalmic composition disposed within the tube, wherein the composition includes:
   i. therapeutic agent; and
   ii. an aqueous vehicle consisting essentially of: a cellulosic polymer at a concentration sufficient by itself to gel the composition wherein the cellulosic polymer is substantially entirely cellulosic ether polymer; one or any combination of excipients selected from the group consisting of borate, tonicity agent and preservative; pH adjusting agent; and water;
wherein:
   i. the composition is substantially free of any anti-oxidant;
   ii. the composition has a pH between 6.0 and 8.5;
   iii. the composition is substantially free of any chemical entity, other than the cellulosic polymer and any of its impurities, that produces any significant amount of free radicals, which would normally degrade the cellulosic polymer within the composition through oxidation reactions;
   iv. the tube is configured for dispensing strips of the composition topically to the eye; and
   v. the viscosity of the composition is at least 5000 mPa*s but no greater than 60000 mPa*s taken at 25° C.

18. A product as in claim 17 wherein the cellulosic polymer is a cellulosic ether polymer.

19. A product as in claim 18 wherein the cellulosic polymer includes hydroxyethyl cellulose.

20. A product as in claim 18 wherein the cellulosic polymer is substantially entirely hydroxyethyl cellulose.

21. A product as in claim 20 wherein the concentration of the HEC in the composition is at least 2.6% but no greater than 4.0%.

22. A product as in claim 21 wherein the therapeutic agent is moxifloxacin.

23. A product as in claim 12 wherein the steroidal anti-inflammatory is dexamethasone.

24. A product as in claim 17 wherein the viscosity of the composition is typically at least 8000 mPa*s but no greater than 35000 mPa*s taken at 25° C.

* * * * *